US008758832B1

(12) United States Patent
Anderson et al.

(10) Patent No.: US 8,758,832 B1
(45) Date of Patent: Jun. 24, 2014

(54) ORAL OR ENTERAL DOSAGE FORMS CONTAINING PHYTOCHEMICALS FROM POMEGRANATES

(75) Inventors: Steve Anderson, Clovis, CA (US); Mark Dreher, Calabasas, CA (US)

(73) Assignee: POM Wonderful LLC, Los Angeles, CA (US)

( * ) Notice: Subject to any disclaimer, the term of this patent is extended or adjusted under 35 U.S.C. 154(b) by 753 days.

(21) Appl. No.: 11/745,440

(22) Filed: May 7, 2007

Related U.S. Application Data

(63) Continuation-in-part of application No. 11/687,480, filed on Mar. 16, 2007, now Pat. No. 7,943,185.

(60) Provisional application No. 60/888,763, filed on Feb. 7, 2007, provisional application No. 60/888,762, filed on Feb. 7, 2007.

(51) Int. Cl.
*A61K 36/185* (2006.01)

(52) U.S. Cl.
USPC ............. 424/725; 424/776; 424/777; 514/27; 514/453

(58) Field of Classification Search
CPC .......................... A61K 36/185; A61K 31/352
USPC ...................... 424/725, 776, 777; 514/27, 453
See application file for complete search history.

(56) References Cited

U.S. PATENT DOCUMENTS

| | | | |
|---|---|---|---|
| 3,943,155 A | 3/1976 | Young | |
| 4,728,522 A | 3/1988 | Wear et al. | |
| 5,484,594 A | 1/1996 | Frangi et al. | |
| 5,891,440 A | 4/1999 | Lansky et al. | |
| 5,912,363 A | 6/1999 | Nafisi-Movaghar et al. | |
| 6,060,063 A | 5/2000 | Lansky et al. | |
| 6,544,581 B1 | 4/2003 | Shrikhande et al. | |
| 7,417,159 B2 | 8/2008 | Galvez et al. | |
| 2001/0030156 A1* | 10/2001 | Gjerde et al. | 210/635 |
| 2005/0165105 A1 | 7/2005 | Bassaganya-Riera | |
| 2007/0254063 A1* | 11/2007 | Aerts et al. | 426/11 |

FOREIGN PATENT DOCUMENTS

WO    WO 2005/097106    * 10/2005

OTHER PUBLICATIONS

Arao, Keisuke, et al., Dietary effect of pomegranate seek oil rich in 9cis, 11 trans, 13cis conjugated linolenic acid on lipid metabolism in obese, hyperlipidemic OLEFT Rats, (2004), 3:24, Nov. 9, 2004, Lipids in Health and Disease.
Aslam, Muhammad Nadeem, et al., Pomegranate as a cosmeceutical source: Pomegranate fractions promote proliferation and procollagen synthesis and inhibit matrix metalloproteinase-1 production in human skin cells, (2006) 311-318, Journal of EthnoPharmacology103.
Van Elswijk, Danny A. et al, Rapid dereplication of estrogenic compounds in pomegranate (*Punica granatum*) using on-line biochemical detection coupled to mass spectrometry, (2004) 233-241, Phytochemistry 65.
Hora, Justin J., et al., Chemopreventive Effects of Pomegranate Seed Oil on Skin Tumor Development in CD1 Mice, 2003, 157-161, Journal of Medicinal Food, J Med Food 6 (3).
Kim, Nam Duek, et al., Chemopreventive and adjuvant therapeutic potential of pomegranate (*Punica granatum*) for human breast cancer, (2002) 71:203-217, Breast Cancer Research and Treatment.
Kohno, Hiroyuki, et al., Pomegranate seed oil rich in conjugated linolenic acid suppresses chemically induced colon carcinogenesis in rats, 2004, 481-486, Cancer Sci, vol. 95.
Lansky, Ephraim Philip, et al., Pomegranate (*Punica granatum*) pure chemicals show possible synergistic inhibition of human PC-3 prostate cancer cell invasion across MatrigelTM, 2005, 121-122, Investigational New Drugs, vol. 23.
Lansky, Ephraim Philip, et al., Possible synergistic prostate cancer suppression by anatomically discrete pomegranate fractions, 2005, 121-122, Investigational New Drugs, vol. 23.
McFarlin, Brian, et al., The Effect of Pomegranate Conjugated Linolenic Acide Supplementation During an Energy-Restricted Diet on Fat Loss and Chronic Inflammation in Previously Obese Mice, Sep. 13, 2006.
Schubert, Shay Y., et al., Antioxidant and eicosanoid enzyme inhibition properties of pomegranate seed oil and fermented juice flavoids, (1999) 11-17, Journal of Ethnopharmacology, 66.
Toi, Masakazu, et al., Preliminary studies on the anti-angiogenic potential potential of pomegranate fractions in vitro and in vivo, (2003) 121-128, Angiogenesis 6.
Yamasaki, Masao, et al., Dietary effect of pomegranate seed oil on immune function and lipid metabolism in mice, (2005), Nutrition.
Yang, Lin, et al al., α-Linolenic acid but not conjugated linolenic acid is hypocholesterolaemic in hamsters (2005) 433-438, Brittish Journal of Nutrition 93.
Das, et al. Studies on the hypoglycaemic activity of *Punica granatum* seed in streptozotocin induced diabetic rats, Phytother Res. 15(7):628-9.(Nov. 2001).
Mehta, R. and Lansky, E.P., Breast cancer chemopreventive properties of pomegranate (*Punica granatum*) fruit extracts in a mouse mammary organ culture, 2004, 13:345-348, European Journal of Cancer Prevention.
Tahraoui, et al. Ethnopharmacological survey of plants used in the traditional treatment of hypertension and diabetes in south-eastern Morocco (Errachidia province), Journal of Ethnopharmacology 110: 105-117 (2007) Available online Sep. 23, 2006.

(Continued)

*Primary Examiner* — Susan Hoffman
(74) *Attorney, Agent, or Firm* — Cotman IP Law Group, PLC

(57) ABSTRACT

Nutraceutical compositions for improved administration of important phytochemicals from pomegranate to a human or animal. More particularly, enables oral or enteral dosage forms containing phytochemicals from pomegranate for administering on a routine basis. In at least one instance the natural contents of a pomegranate are encapsulated into a pill form or concentrated juice that provides for more efficient administration than eating a pomegranate but contains the same key ingredients present in the fruit. Enables the recipient to receive the benefits of the fruit but allows for the dosages to be taken in pill or concentrated juice form. Composition is chemically similar or equal to a natural pomegranate but is in a powder, pill or concentrated liquid form.

18 Claims, No Drawings

(56) References Cited

OTHER PUBLICATIONS http://www.sciencegeek.net/APchemistry/organic/ochem.shtml—accessed Oct. 16, 2009.

Seeram et al. "Bioavailability of ellagic acid in human plasma after consumption of ellagitannins from pomegranate (*Punica granatum* L.) juice", Clinica Chimica Acta 348 (2004) 63-68.

Seeram, et al., "Pomegranate Juice Ellagitannin Metabolites Are Present in Human Plasma and Some Persist in Urine for Up to 48 Hours", Journal of Nutrition, 2006, 2481-2485.

Seeram, et al. "Pomegranate Juice and Extracts Provide Similar Levels of Plasma and Urinary Ellagitannin Metabolites in Human Subjects" Journal of Medicinal Food, 11 (2) 2008, 390-394.

D. Syed, et al. "Photochemopreventive Effect of Pomegranate Fruit Extract on UVA-mediated Activation of Cellular Pathways in Normal Human Epidermal Keratinocytes" Photochemistry and Photobiology, 2006, 82: 398-405.

Adams, et al. "Pomegranate Juice, Total Pomegranate Ellagitannins, and Punicalagin Suppress Inflammatory Cell Signaling in Colon Cancer Cells" Journal of Agricultural and Food Chemistry, 2006, 54, 980-985.

V. Adhami, et al. "Polyphenols from green tea and pomegranate for prevention of prostate cancer" Free Radical Research, Oct. 2006; 40(10): 1095-1104.

S. Kasimsetty, et al. "Effects of Pomegranate Chemical Constituents/Intestinal Microbial Metabolites on CYP1B1 in 22Rv1 Prostate Cancer Cells" Journal of Agriculture and Food Chemistry, 2009, 57, 10636-10644.

Sartippour, et al., "Ellagitannin-rich pomegranate extract inhibits angiogenesis in prostate cancer in vitro and in vivo" International Journal of Oncology, 2008, 32:475-480.

Rettig, et al. "Pomegranate extract inhibits androgen-independent prostate cancer growth through a nuclear factor-KB-dependent mechanism" Molecular Cancer Therapy, 2008; 7(9): 2662-71.

Seeram, et al. "Pomegranate Ellagitannin-Derived Metabolites Inhibit Prostate Cancer Growth and Localize to the Mouse Prostate Gland" Journal of Agricultural and Food Chemistry, 2007, 55, 7732-7737.

Hong, et al. "Pomegranate polyphenols down-regulate expression of androgen-synthesizing genes in human prostate cancer cells overexpressing the androgen receptor" Journal of Nutritional Biochemistry, 2008, 8 pages.

J. Trombold, et al. "Ellagitannin Consumption Improves Strength Recovery 2-3 d after Eccentric Exercise" The American College of Sports Medicine, 2010, 493-498.

B. Fuhrman, et al. "Pomegranate juice polyphenols increase recombinant paraoxonase-1 binding to high-density lipoprotein: Studies in vitro and in diabetic patients" Nutrition 26 (2010) 359-366.

J. Khateeb, et al. "Paraoxonase 1 (PON1) expression in hepatocytes is upregulated by pomegranate polyphenols: A role for PPAR" Atherosclerosis, 2009, 7 pages.

M. Davidson, et al. "Effects of Consumption of Pomegranate Juice on Carotid Intima-Media Thickness in Men and Women at Moderate Risk for Coronary Heart Disease" American Journal of Cardiology, 2009, 936-942.

O. Rozenberg, et al. Pomegranate juice sugar fraction reduces macrophage oxidative state, whereas white grape juice sugar fraction increases it Atherosclerosis, 188 (2006) 68-76.

Mattiello, et al. "Effects of Pomegranate Juice and Extract Polyphenols on Platelet Function" Journal of Medicinal Food, 12 (2) 2009, 7 pages.

Sumner, et al. "Effects of Pomegranate Juice Consumption on Myocardial Perfusion in Patients With Coronary Heart Disease" American Journal of Cardiology, 2005, 5 pages.

M. Aviram, et al. "Pomegranate juice consumption inhibits serum angiotensin converting enzyme activity and reduces systolic blood pressure" Atherosclerosis, 158 (2001) 195-198.

M. Aviram, et al. "Pomegranate Phenolics from the Peels, Arils, and Flowers Are Antiatherogenic: Studies in Vivo in Atherosclerotic Apolipoprotein E-Deficient (E0) Mice and in Vitro in Cultured Macrophages and Lipoproteins" Journal of Agricultural and Food Chemistry, 2008, 56, 1148-1157.

Shiner et al. "Macrophage paraoxonase 2 (PON2) expression is upregulated by pomegranate juice phenolic anti-oxidants via PPAR and AP-1 pathway activation" Atherosclerosis, 2007, 9 pages.

de Nigris, et al. "Effects of a Pomegranate Fruit Extract rich in punicalagin on oxidation-sensitive genes and eNOS activity at sites of perturbed shear stress and atherogenesis" Cardiovascular Research, 2007, 73, 414-423.

de Nigris, et al."Pomegranate juice reduces oxidized low-density lipoprotein downregulation of endothelial nitric oxide synthase in human coronary endothelial cells" Nitric oxide, 2006 15 259-263.

L. Ignarro, et al. "Pomegranate juice protects nitric oxide against oxidative destruction and enhances the biological actions of nitric oxide" Nitric oxide, 2006, 15, 93-102.

de Nigris et al. "Beneficial effects of pomegranate juice on oxidation-sensitive genes and endothelial nitric oxide synthase activity at sites of perturbed shear stress" Proceedings of the National Academy of Sciences, 2005, vol. 102, No. 13, 6 pages.

Rosenblat, et al. "Pomegranate Byproduct Administration to Apolipoprotein E-Deficient Mice Attenuates Atherosclerosis Development as a Result of Decreased Macrophage Oxidative Stress and Reduced Cellular Uptake of Oxidized Low-Density Lipoprotein" Journal of Agricultural and Food Chemistry, 2006, 54, 1928-1935.

de Nigris, et al. "The influence of pomegranate fruit extract in comparison to regular pomegranate juice and seed oil on nitric oxide and arterial function in obese Zucker rats" Nitric Oxide, 2007 17, 50-54.

Kaplan, et al. "Pomegranate Juice Supplementation to Atherosclerotic Mice Reduces Macrophage Lipid Peroxidation, Cellular Cholesterol Accumulation and Development of Atherosclerosis" Journal of Nutrition, 2001, 2082-2089.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007, 83: 882-888.

Lorean et al. "Maternal Dietary Supplementation with Pomegranate Juice Is Neuroprotective in an Animal Model of Neonatal Hypoxic-Ischemic Brain Injury" Pediatric Research, 2005, vol. 57, No. 6, 7 pages.

Shah, et al. "Pomegranate juice decreases amyloid load and improves behavior in a mouse model of Alzheimer's disease" Neurobiology of Disease, 2006, Abstract.

D. Bialonska, et al. "Urolithins, Intestinal Microbial Metabolites of Pomegranate Ellagitannins, Exhibit Potent Antioxidant Activity in a Cell-Based Assay" Journal of Agriculture and Food Chemistry, 2009, 57, 10181-10186.

Y. Zhang, et al. "Absence of Pomegranate Ellagitannins in the Majority of Commercial Pomegranate Extracts: Implications for Standardization and Quality Control" Journal of Agricultural and Food Chemistry, 2009, 57, 7395-7400.

Y. Zhang, et al. "International Multidimensional Authenticity Specification (IMAS) Algorithm for Detection of Commercial Pomegranate Juice Adulteration", Journal of Agricultural and Food Chemistry, 2009, 9 pages.

S. Madrigal-Carballo, et al. "Pomegranate (*Punica granatum*) supplements: authenticity, antioxidant and polyphenol composition" Journal of Functional Foods, 2009, 6 pages.

K. Martin et al. "Development of a novel pomegranate standard and new method for the quantitative measurement of pomegranate polyphenols" Journal of Science of Food and Agriculture, 2009; 89:157-162.

N. Seeram, et al. "Comparison of Antioxidant Potency of Commonly Consumed Polyphenol-Rich Beverages in the United States" Journal of Agricultural and Food Chemistry, 2008, 56, 1415-1422.

Rosenblat, et al. "Consumption of polyphenolic-rich beverages (mostly pomegranate and black currant juices) by healthy subjects for a short term increased serum antioxidant status, and the serum's ability to attenuate macrophage cholesterol accumulation" Food & Function, 2010, 1, 99-109.

G. Borges, et al. "Comparison of the polyphenolic composition and antioxidant activity of European commercial fruit juices" Food & Function, 2010, 11 pages.

(56) References Cited

OTHER PUBLICATIONS

A. Sundararajana, et al. "Influenza virus variation in susceptibility to inactivation by pomegranate polyphenols is determined by envelope glycoproteins" Elsevier, 2010 (1-9).

R. Oliveira, et al. "Effects of feeding polyphenols from pomegranate extract on health, growth, nutrient digestion, and immunocompetence of calves" American Dairy Science Association, 2010, 93:4280-4291.

M. Haidari, et al. "Pomegranate(*Punicagranatum*) purified polyphenol extract inhibits influenza virus and has a synergistic effect with oseltamivir" Phytomedicine, 2009, 10 pages.

D. Bialonska, et al. "The influence of pomegranate by-product and punicalagins on selected groups of human intestinal microbiota" International Journal of Food Microbiology, 140 (2010) 175-182.

M. Reddy, et al. "Antioxidant, Antimalarial and Antimicrobial Activities of Tannin-Rich Fractions, Ellagitannins and Phenolic Acids from *Punica granatum* L." Planta Medica, 2007, 7 pages.

M. Shukla, et al. "Consumption of hydrolyzable tannins-rich pomegranate extract suppresses inflammation and joint damage in rheumatoid arthritis" Nutrition, 24, 2008, 733-743.

Z. Rasheed, et al. "Polyphenol-rich pomegranate fruit extract (POMx) suppresses PMACI-induced expression of pro-inflammatory cytokines by inhibiting the activation of MAP Kinases and NF-κB in human KU812 cells" Journal of Inflammation, 2009, 12 pgs.

Glycaemic Index Research Service "A Study to Measure the Glycaemic Index Value of Pomegranate Juice" The School of Molecular and Microbial Bio-sciences at Sydney University, Mar. 2009, 22 pgs.

B. McFarlin, et al. "Pomegranate seed oil consumption during a period of high-fat feeding reduces weight gain and reduces type 2 diabetes risk in CD-1 mice" British Journal of Nutrition, 2008, 6 pages.

W. Rock, et al. "Consumption of Wonderful Variety Pomegranate Juice and Extract by Diabetic Patients Increases Paraoxonase 1 Association with High-Density Lipoprotein and Stimulates Its Catalytic Activities" Journal of Agricultural and Food Chemistry, 2008, 56, 8704-8713.

M. Rosenblat, et al. "Anti-oxidative effects of pomegranate juice (PJ) consumption by diabetic patients on serum and on macrophages" Atherosclerosis, 187 (2006) 363-371.

Q. Zhang, et al. "Dietary antioxidants improve arteriogenic erectile dysfunction" International Journal of Andrology, 33, 2010, 1-11.

K. Azadzoi, et al."Oxidative Stress in Arteriogenic Erectile Dysfunction: Prophylactic Role of Antioxidants" Journal of Urology, 2005, vol. 174, 386-393.

Forest, et al. "Efficacy and safety of pomegranate juice on improvement of erectile dysfunction in male patients with mild to moderate erectile dysfunction: a randomized, placebo-controlled, double-blind, crossover study" International Journal of Impotence Research, 2007, 1-4.

S. Strum, et al. "Pomegranates and Prostate Health: A Research Report", PCRI Insights, 2008, vol. 11: No. 3, 36 pages.

A. McCutcheon, et al. "Scientific and Clinical Monograph for POM Wonderful Pomegranate Juice" American Botanical Council, 2008, 20 pgs.

M. Aviram, et al. "Pomegranate juice flavonoids inhibit low-density lipoprotein oxidation and cardiovascular diseases: Studies in atherosclerotic mice and in humans" Drugs Under Experimental and Clinical Research XXVIII, 2003, 15 pages.

M. Warren, et al. "Pomegranate's Ancient Roots to Modern Medicine, Pomegranates: Ancient Roots to Modern Medicine" Taylor and Francis, 2006, 158-166.

D. Heber, et al. "Safety and Antioxidant Activity of a Pomegranate Ellagitannin-Enriched Polyphenol Dietary Supplement in Overweight Individuals with Increased Waist Size" Journal of Agricultural and Food Chemistry, 2007, 55, 10050-10054.

D. Farkas, et al. "Pomegranate Juice Does Not Impair Clearance of Oral or Intravenous Midazolam, a Probe for Cytochrome P450-3A Activity: Comparison With Grapefruit Juice" Journal of Clinical Pharmacology, 2007; 47;286-294.

F. Afaq, et al. "Protective effect of pomegranate-derived products on UVB-mediated damage in human reconstituted skin" Experimental Dermatology, 2009.

M. Abu Zaid, et al. "Inhibition of UVB-mediated Oxidative Stress and Markers of Photoaging in Immortalized HaCaT Keratinocytes by Pomegranate Polyphenol Extract POMx" Photochemistry and Photobiology, 2007.

D Pérez et al., Wine, Diet, Antioxidant Defenses and Oxidative Damage. Annals of the New York Academy of Sciences (2002),957:136-145.

KJ Joshipura, et al., The Effect of Fruit and Vegetable Intake on Risk for Coronary Heart Disease. Annals of Internal Medicine (2001),134:1106-1114.

http://www.wonderulpomegranateresearch.com/featured, accessed Jun. 28, 2011.

Rosenblat et al. "Pomegranate Juice Protects Macrophages from Triglyceride Accumulation: Inhibitory Effect on DGAT1 Activity and on Triglyceride Biosynthesis" Ann Nutr Metab 2011;58:1-9.

\* cited by examiner

ORAL OR ENTERAL DOSAGE FORMS
CONTAINING PHYTOCHEMICALS FROM
POMEGRANATES

This application is a continuation in part of U.S. Utility patent application Ser. No. 11/687,480 filed Mar. 16, 2007, now U.S. Pat. No. 7,943,185, and claims benefit of U.S. Provisional Patent Application Ser. No. 60/888,763 filed Feb. 7, 2007, and Ser. No. 60/888,762 filed Feb. 7, 2007.

BACKGROUND OF THE INVENTION

1. Field of the Invention

One or more embodiments of the invention described herein pertain to processes for making nutraceutical compositions for improved administration of phytochemicals from pomegranate to a human or animal and methods of use thereof. More particularly, but not by way of limitation, one or more embodiments of the invention enable oral or enteral dosage forms containing phytochemicals from pomegranate in a quantity that reflects that of the natural fruit itself.

2. Description of the Related Art

Pomegranates have a long history of use. The pomegranate is an ancient food native to the Middle East. The historical record shows that it was among the first fruits to be cultivated.

Pomegranates are popularly consumed as fresh fruits, as beverages (e.g., juices and wines), and as food products (e.g., jams and jellies). Commercial sources of pomegranate juice are obtained namely by a hydrostatic pressing process of whole fruits whereby various types of phytochemicals contained within the pomegranate are extracted into juice form.

The consumption of phytochemical-rich diet has been associated with a reduced risk of chronic human illnesses such as certain types of cancers, inflammation, and cardiovascular and neurodegenerative diseases. The pomegranate has recently been acclaimed for its health benefits and for its disease-fighting potential. There are studies concerning associated beneficial effects of pomegranate phytochemicals, including polyphenols, proanthocyanidins, hydrolysable tannins, etc. Hence it is desirable to gain whatever beneficial effects might be present by consuming pomegranate and its phytochemicals. The oral route is the least invasive, most convenient route for administering pomegranate phytochemicals on a routine basis. However, the pomegranate fruit is a difficult fruit to consume and certain pomegranate phytochemicals may lose their health beneficial effects by undergoing chemical reactions into less bioavailable and/or less bioactive forms during processing and storage of juices and extracts.

For example, a major polyphenol antioxidant called punicalagin hydrolyzes into ellagic acid during processing and storage of juices and extracts, its ability to offer antioxidant potency to the body is wasted since free ellagic acid has not been found to be bioavailable. But when punicalagins are preserved and then consumed, they offer the researched health benefits of ellagic acid, which can be absorbed into the bloodstream in this way. Punicalagins are 100% water-soluble, highly bioavailable, and shown to possess a high absorption rate up to 95%. Not only do punicalagins offer antioxidant activity on their own, they can break up into smaller polyphenols that are also absorbed into the body. Punicalagins are one important component of pomegranate polyphenols, but the total composition of the polyphenols themselves is a complex mixture of numerous other components.

Predominant types of pomegranate polyphenolic compounds are hydrolyzable tannins, which are found in the peels (rind, husk, or pericarp), membranes, and piths of the fruit. Hydrolyzable tannins, of which punicalagin is classified, are susceptible to enzymatic and non-enzymatic hydrolysis. Hydrolyzable tannins are gallic acid and ellagic acid esters of core molecules that consist of polyols such as sugars. During hydrolysis, gallotannins yield gallic acid and glucose while ellagitannins yield ellagic acid and glucose. The reported soluble polyphenol content in pomegranate juice varies within the limits of 0.2 to approximately 1.5% and ellagic acid was measured in commercial juices around 100 to 3000 mg/L.

For the reasons above, many of products claiming to contain "natural pomegranate" may in fact lack key ingredients or phytochemicals that may have health beneficial effects. Hence there is a need to find ways to concentrate pomegranate phytochemicals, including polyphenol antioxidants such as punicalagins and its isomers, in their bioavailable and bioactive forms that may be otherwise lost during the processing and storage of juices and extracts.

For at least the limitations described above there is a need for processes for producing an oral or enteral dosage form containing key phytochemicals from pomegranates.

BRIEF SUMMARY OF THE INVENTION

One or more embodiments of the invention are nutraceutical compositions for improved administration of important phytochemicals from pomegranate to a human or animal. More particularly, one or more embodiments of the invention enable oral or enteral dosage forms containing phytochemicals from pomegranate for administering on a routine basis. In at least one instance the natural contents of a pomegranate are encapsulated into a pill form or concentrated juice that provides for more efficient administration than eating a pomegranate but contains the same key ingredients present in the fruit. Hence the composition described herein enables the recipient to receive the benefits of the fruit but allows for the dosages to be taken in pill or concentrated juice form. Put simply the composition is chemically similar or equal to a natural pomegranate but is in a powder, pill or concentrated liquid form. To formulate the juice whole pomegranates are sliced to release the arils and pressed. The concentrated liquid is then produced by conducting a further round of pressing on the byproducts that remain after the juice is extracted and hence the liquid concentrate is made from the de-juiced byproducts that remain after the first pressing.

One or more embodiments of the invention include enteral or oral dosage forms for administration on a routine basis of the nutraceutical composition containing pomegranate phytochemicals, including punicalagins, its isomers, and other high molecular weight polyphenols. Particularly suitable is a dosage or serving for administration containing a dry composition of pomegranate which contains same compounds as pomegranate juice, or the fruit itself optionally differing only in higher proportional content of polypheonols, particularly punicalagin and its isomers.

The liquid is concentrated such that one-teaspoon contains the polyphenol content of roughly one 8 oz. glass of pomegranate juice. Either the powder extract or the concentrated liquid may be mixed into any other volume of liquid to form various mixtures. A consumer or manufacture may, for instance, create a drink such as a tea or any other mixture that once mixed contains polyphenols equivalent to an 8 oz. glass of juice. Other variations in polyphenol content are controllable by varying the amounts of powder or liquid concentrate introduced into the mixture.

Generally speaking the process for extracting the polyphenols to make the powder or liquid concentrate uses a two step "food type" process: (1) extraction of polyphenols from pomegranate fruit, and (2) purification of the extract to produce pomegranate food polyphenol extract powder. Extraction is performed using a mixture whole and juice-pressed pomegranate fruit and separated arils. Each of these process steps is briefly described further below. Aqueous Extract ion: The mixture of whole and juice-pressed pomegranate fruit and separated arils are milled and screened to remove seeds. The de-seeded fruit (mash) is immersed in hot water and treated with enzymes (pectinase) to accelerate the release of polyphenols from the fruit. Mash solids are removed using a decanter. The resulting liquid is pasteurized and ultra-filtered to remove insoluble solids. The filtered aqueous extract is concentrated in an evaporator to produce a concentrate high in natural polyphenols which are similar in range to the polyphenols in pomegranate juice. The liquid extract concentrate is stored in a secure, refrigerated warehouse pending purification Ethanol in Water Purification. Polyphenols are recovered from the extract concentrate using FDA food-grade resins. Extract concentrate, diluted with water, is passed through resin columns which preferentially adsorbs polyphenols minus most of the anthocyanins from the extract liquid. The resins do not chemically modify the polyphenols; they reversibly adsorb and desorb the polyphenols with their original chemical structure remaining unchanged. Non-phenol compounds, such as sugars, organic acids, cellulose, and other carbohydrates, pass unadsorbed through the resin column. Polyphenols adsorbed on the resin are recovered (de-adsorbed) using ethanol in water. The recovered polyphenols are concentrated by completely removing ethanol. The remaining polyphenol water solution is dried to produce a pomegranate food polyphenol extract powder.

One or more embodiments for enteral or oral dosage forms for administration of the nutraceutical composition may preserve or stabilize certain pomegranate phytochemicals, including punicalagins and its isomers, in their bioavailable and bioactive forms that may be otherwise lost during the processing and storage of juices and extracts. Accordingly, the dosage used in embodiments of the invention may be applied in any suitable solid or semisolid form such as capsule, pill, powder, tablet, and the like.

Other objects, features and advantages of the embodiments of the invention will become apparent to those skilled in the art from the following detailed description. It is to be understood, however, that detailed description and specific examples, while indicating preferred embodiments of the invention, are given by way of illustration and not limitation. Many changes and modifications within the scope of the invention may be made without departing from the spirit thereof, and the invention includes all such modifications and equivalents thereof.

DETAILED DESCRIPTION

Compositions and processes for making oral or enteral dosage forms containing phytochemicals from pomegranate and methods of use thereof will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

All patents, patent applications, and publications cited herein are incorporated by reference in their entirety. This specifically includes, the following copending applications:

U.S. patent application Ser. No. 09/294,307 (filed Apr. 19, 1999); U.S. patent application Ser. No. 09/998,883 (filed Nov. 19, 2001); U.S. patent application Ser. No. 10/701,918 (filed Nov. 4, 2003); U.S. patent application Ser. No. 11/252, 842 (filed Oct. 18, 2005); U.S. patent application Ser. No. 60/784,861 (filed Mar. 21, 2006); U.S. patent application Ser. No. 11/137,248 (filed May 24, 2005); U.S. patent application Ser. No. 60/782,437 (filed Mar. 15, 2006)

The term nutraceutical as used herein denotes usefulness in both the nutritional and pharmaceutical field of application. Thus, the nutraceutical compositions refer to any compound or chemicals, including but not limited to pomegranate phytochemicals, that can provide dietary or health benefits when consumed by humans or animals. The nutraceutical compositions can find use as supplements or additives to food and beverages, and as pharmaceutical formulations for enteral or parenteral application that may be solid or semisolid formulations such as capsules or tablets, or liquid formulations, such as solutions or suspensions. As will be evident from the foregoing, the term nutraceutical composition also comprises supplement including pomegranate compositions containing at least one component selected from phytochemicals including punicalagin, punicalin, other ellagitannins, and gallotannins, as well as food and beverage compositions containing the aforesaid active ingredients.

As used herein, the term "phytochemicals" refers collectively to compounds which are naturally-occurring in the pomegranate and to reaction products and metabolites of these compounds, which are considered to have a beneficial effect on the human or animal health. Examples of such phytochemicals include, but not limited to phenolics, polyphenols, organic and phenolic acids, sterols and triterpenoids, fatty acids and triglycerides, and alkaloids.

As used herein, the term "polyphenols" refers generally to a family of compounds in the pomegranate and includes phenols and polyphenols. Phenols are a class of chemical compounds consisting of a single phenol unit in their structure. Although similar to alcohols, phenols have unique properties including relatively higher acidities due to the aromatic ring tightly coupled to the oxygen and a relatively loose bond between the oxygen and the hydrogen. Examples of phenolic compounds within this group include ellagic and gallic acid. Polyphenols are a group of compounds, characterized by the presence of more than one phenolic group. Polyphenols include tannins (e.g., ellagitannins and gallotannins), flavonoids (e.g., anthocyannins and isoflavones) and stilbenes (e.g., resveratrol).

As used herein, the term "pomegranate juice" refers to the juice that is substantially obtained from the arils of the pomegranate by crushing and squeezing the whole fruit itself.

As used herein, the term "pomegranate solids" refers to any one or a combination of the pericarp, the inner membrane and seeds of a pomegranate.

It has been discovered that hydrolyzable tannins are susceptible to enzymatic and non-enzymatic hydrolysis during processing and storage of pomegranate juices and extracts. More particularly, a predominant pomegranate hydrolyzable tannin, punicalagin, hydrolyzes into ellagic acid during processing and storage of juices and extracts thus its ability to offer antioxidant potency to the body may be wasted. Punicalagin is a powerful antioxidant and shown to be 100% water-soluble and highly bioavailable. The researched health benefits of ellagic acid may only be obtained when punicalagins are preserved and then absorbed into the bloodstream after an oral or enteral route and break up into smaller polyphenols. While the antioxidant and other beneficial health effects of the pomegranate are due to the presence of polyphenols, the presence of other phytochemical compounds in pomegranate, or the synergistic effect of these phytochemicals, may also be responsible for the antioxidant and other beneficial health effects of pomegranate.

The polyphenols are responsible for a bitter taste and astringent quality of the pomegranate juice. It has been discovered that the taste of polyphenols and the other constituents of pomegranate significantly limit the concentration of active ingredients in liquid form for food and beverage applications. The susceptibility of hydrolyzed tannins to hydrolysis and other phytochemicals of pomegranate to undesirable chemical reactions also significantly limit the concentration of active ingredients in pomegranate juices and extracts for food and beverage applications. The separation process which makes us of various chromatographic techniques to separate and purify polyphenols from the fruit or byproducts of the fruit will now be described.

Separation Process

Polyphenols are a mixture of substances of very different molecular weight and polarity. They are known to be soluble or partly soluble in polar solvents or admixtures thereof (e.g., water, ethanol, methanol, acetone, ethyl acetate).

The adsorption mechanism typically relies upon non-specific dipole-dipole interactions between the separation medium and the components of the liquid extract. The eluent (solvent) carries molecules faster those of which are less tightly bound to the medium. In preferred embodiments the separation medium is a chromatographic medium acceptable for use in the food industry. The medium is conveniently supported in a large (preparative) scale chromatographic column. Separation column resin beds up to 4 feet in diameter and 4 feet in height are described herein, and it is contemplated that substantially larger diameter resin beds may be utilized without the need for internal flow distributing structures, thereby substantially increasing the total output volume from the system.

The separation medium may include a synthetic polymeric adsorbent resin. Generally these synthetic polymeric adsorbents take the form of non-ionic macroreticular resins that adsorb and release ionic and polar molecules (compounds) through hydrophobic and polar interactions; these are usually employed under isocratic conditions (i.e., only a single eluent of fixed composition is used). Such polymeric resins are usually derived from a synthetic hydrophobic polyaromatic resin such as cross-linked polyvinylbenzene (polystyrene) and polydivinylbenzene. These resins are manufactured under trade names such as Amberchrom™, Amberlite™, Diaion™, and Dowex™. One advantage of the polystyrene-divinylbenzene copolymer resin is that the polyphenols are especially well adsorbed when dissolved in water or dilute aqueous C1-C3 alkanol (e.g. 2% v/v ethanol), preferably at the nominal operating range of 100° to 140° F.

It may be possible to use natural polymeric media, such as microparticulate cellulose which is particularly well suited for the separation of nucleotides, sugars, amino acids and polyphenols. Potential drawbacks to the use of microparticulate cellulose or derivatives thereof, are swelling in an aqueous environment and/or compressibility under pressure.

Other alternatives are dextran polymers (e.g. Sephadex™, Pharmacia UK) or agarose beads (e.g., Sepharose™, Pharmacia, UK).

In one or more embodiments, temperature range for operating the separation process is in the range of 100° to 140° F. Less preferred is using the separation medium at the temperature below 100° F. which alters the adsorption characteristics of polyphenols and other phytochemicals of interest.

In one or more embodiments, the flow rate through the separation medium is in the range one to three bed volumes an hour, optimally two bed volumes per hour. A bed volume is the amount of the adsorbent resin in a separation medium. The volume and total time of flow of a particular feed stream into the column can be controlled by the desired output and the input stream. The optimal flow rate enables the separation medium to sequester polyphenols and other phytochemicals of interest, and rinse out the unbound material.

For rinsing step in one or more embodiments, a dilute aqueous alcohol is passed through the separation medium to remove unbound material (e.g., sugars, proteins, fibers, enzymes, carbohydrates). When obtaining a high purity of polyphenols in the pomegranate dry composition is desired, it is preferred that this rinsing step performed prior to the elution of polyphenols. Optionally, the rinse step may include back flushing the separation medium with a dilute aqueous alcohol to remove any insoluble material that may collect on the top of the separation medium. Dilute aqueous alcohol is any aqueous solution containing alkanol having one to four carbon atoms and of less than about 5% v/v, more preferable 2% v/v. Ethanol is preferred alkanol since it is approved for food use. Less preferable is water, which is not as effective at getting unbound material out of the separation medium and reduces the purity of polyphenols in the pomegranate dry composition.

For an elution of polyphenols and other phytochemicals of interest from the separation medium in one or more embodiments, eluting solvents may be any polar solvent which are accepted for the preparation of food (e.g., water, methanol, ethanol, acetone, ethyl acetate, methylene dichloride, chloroform or mixtures thereof). In one or more embodiments, the eluting solvent is a concentrated aqueous alcohol containing alkanol having one to four carbon atoms and of at least about 5% v/v, more preferably alkanol is ethanol. More preferred is aqueous ethanol of no more than 20% v/v which does not require the need of an expensive explosion-proof equipment.

Pomegranate Dry Composition

A pomegranate dry composition is obtained from the pomegranate solid, in accordance with the methods disclosed herein, which has a substantially higher polyphenol content than other known methods. This is particularly true with respect to the higher molecular weight polyphenols and, in particular, punicalagins. In addition to punicalagin, other high molecular weight polyphenols characterized in the pomegranate dry composition include ellagitannin and other hydrolysable tannins, such as punicortein A, punicalin, pedunculagin, and gallotannin dimers and trimers. Once obtained the dry composition may be filled into capsules for distribution in pill form or mixed into various liquids to increase the polyphenol content of a particular liquid.

Punicalagins and other phytochemicals of pomegranate may remain stable when processed and stored in the pomegranate dry composition. Thus, less of hydrolysable tannins, for example, in the dry composition become hydrolyzed to nonbioavailable and/or less bioactive forms. Thus embodiments of the invention may be used in oral or enteral dosage form as a nutraceutical composition including, for instance, a pomegranate dry composition. This nutraceutical composition may be administered in oral, pill or liquid form.

Accordingly, methods are provided for producing a pomegranate dry composition containing phytochemicals from the pomegranate solids. The pomegranate dry composition produced from the methods disclosed herein differs from the commercially-available pomegranate juice in that the concentrate is substantially derived from the pomegranate solid, whereas pomegranate juice is substantially derived from the arils that surrounds the pomegranate seeds. The pomegranate dry composition is characterized as powder and containing polyphenols, particularly, high molecular weight polyphenols, such as punicalagin.

In one embodiment of the invention, the method includes providing any one of a combination of pomegranate solids. For instance, one may make use of the pericarp, inner membrane and seeds to create a mixture comprising the pomegranate solids in an aqueous solution. In one or more embodiments of the invention, the mixture of the pomegranate solids may be created by adding water in an amount that is about 20-80% w/v, and more preferably about 50% w/v, of the pomegranate solids. The mixture is preferably crushed or milled to create a rough grind of pomegranate solids dispersed in the aqueous solution.

Alternatively, the starting materials for production of the concentrate are solids from the husks and residual fruits that remain after the first or second pressing of whole fruits in the production of the juice concentrate. Both powder or concentrated liquid forms may be made with these materials. In another embodiment of the invention, the mixture of the solids may be created by adding water in an amount that is about 20-80% w/v, and more preferably about 50 w/v, of the solids. The mixture may be crushed or milled to create a rough grind of pomegranate solids dispersed in the aqueous solution.

The mixture is then heated to a temperature of about 60° F. to 210° F. Various ranges are operative for purposes of implementing the invention. One embodiment of the invention for instance uses a range of about 85° F. to 185° F. while alternatives may make use of ranges of about 110° F. to 160° F. The temperature to which the mixture is heated depends upon the selection of enzymes, or combination of enzymes, that is added to the mixture. The mixture is heated to a temperature that permits the maximum catalysis of the enzyme or combination of enzymes.

Alternatively, enzymes may be added before the mixture is heated. Thus, the order of the steps of heating the mixture and adding the enzymes is not meant to be limiting, so long as the mixture is heated to a temperature that permits the enzymes to at least partially degrade the pomegranate solids and liberate phytochemicals from the plant tissues and/or cells. Once liberated, the phytochemicals may react and/or polymerize to create new phytochemical compounds or reaction products.

Enzymes suitable for use in accordance with this embodiment of the invention include those that are capable of at least partially degrading the plant tissue or cells to liberate the phytochemicals from the pomegranate solids. Such enzymes include any one or a combination of pectinase, cellulase, hemicellulase, amylase, arabanase, and other hydrolyzing enzymes, to name a few. The enzymes added to the mixture may be naturally-occurring or synthetic. They may be derived from any one or a combination of sources, such as animal, plant, fungal, and bacterial sources. The amount of the enzyme or combination of enzymes added to the mixture depends on the temperature of the mixture and the amount of pomegranate solids present in the mixture.

After enzymes are added, the mixture is maintained at a temperature for a time sufficient to allow at least partial degradation of the pomegranate solids. The temperature and length of time required depends on the type of enzymes added to the mixture, the rate of enzyme catalysis and the amount of the pomegranate solids contained in the mixture.

Thus, in one preferred embodiment, a combination of pectinase, cellulase and hemicellulase enzymes are added to the mixture, which is heated to a temperature of about 60° F. to 210° F. One embodiment of the invention for instance makes use of a heat of about 110° F. to 160° F. whereas other embodiments of the invention stop at 120° F. The mixture is maintained at these temperatures, typically with agitation or stirring, for about 45-195 minutes. Variations are feasible however as in one embodiment of the invention the mixture is maintained for 45-75 minutes. At least one instance 60 minutes is thought to be an effective amount of time for maintaining the mixture at temperature.

After the enzymes have at least partially degraded the pomegranate solids, the residual insoluble solid materials are removed from the mixture. Optionally, a clarification agent, such as bentonite, may be added before the step of removing the residual insoluble materials from the mixture. The removal of residual insoluble materials from the mixture may be accomplished by filtration, centrifugation, chromatographic techniques, and other techniques. Filtration techniques suitable for the practice of the methods disclosed herein include micro-filtration at a molecular weight cut-off of at least 100,000 Da, and preferably of about 100,00 to 200,000 Da. The mixture may be passed through more than one filtration step, e.g., first step with filtration at a higher molecular weight cut-off then one or more subsequent steps with filtration at a lower molecular weight cut-off. After filtration, the resulting liquid extract is about 2° to 8° Brix.

The resulting liquid extract may be pasteurized at a temperature and for a length of time sufficient to kill microorganisms that could cause disease, spoilage or undesired fermentation. In one embodiment of the invention, the extract may be pasteurized at a temperature of about 140° F. to 280° F., preferably of about 195° F. to 240° F., and optimally of about 205° F. The pasteurization may also denature the remaining enzymes that were added to the mixture.

In one or more embodiments of the invention, the filtered liquid extract may be further concentrated to, for example, 15°-20° Brix before the filtered liquid extract is being applied to a separation medium. The concentration of the liquid extract may be accomplished with any suitable evaporator or distillation methodology and apparatus. For example, the liquid extract may be concentrated in a rising-film plate evaporator.

The filtered liquid extract is passed through a separation medium, which is then rinsed with a dilute aqueous alcohol to remove unbound material. Eluted dilute aqueous alcohol containing unbound material may be collected and can be further processed, for example, for use in foods as flavors. The polyphenols bind to the separation medium and may be eluted with a solvent, preferably a concentrated aqueous ethanol.

In one or more embodiments, the concentrated aqueous alcohol eluate containing polyphenols may be processed through a conventional distillation unit to remove the alcohol. Alcohol may be recovered from distillation and reused in the subsequent cycles of rinse and/or elution steps.

The resulting liquid eluate containing polyphenols may be dried by employing any suitable drying methodology and apparatus, which includes the steps including a rotary evaporator under reduced pressure and followed by further drying in a desiccator. Another drying methodology is lyophilization, which comprises freezing the liquid extract and then drying the same under high vacuum conditions in order to allow the water in the solid state to sublimate at low temperature. That is, the water is removed from the material by passing directly from the solid to the gaseous state, without passing through the liquid state. A drying methodology used in accordance with at least one embodiment of the invention is tray drying or spray drying the liquid eluate containing polyphenols. After drying step, these results in pomegranate dry composition in a powder form and may be utilized in other embodiments of the invention.

Enteral or Oral Dosage Unit

The purity of polyphenols in the pomegranate dry composition may influence the number and size of dosage unit. The amount of pomegranate dry composition may varies in the preparation of dosage unit. In one or more embodiments of the invention, it is preferred that polyphenol content in the dry composition is of a sufficiently high purity that the dosage unit is delivered in a single oral or enteral form that is conveniently administered to human subject that is equivalent to polyphenol content of 8 oz. freshly made pomegranate juice. The method of making pomegranate dry composition with high purity of polyphenols (e.g, about 90%) is disclosed herein enables a convenient single oral or enteral dosage unit that is equivalent to polyphenol content of approximately 8 oz. freshly made pomegranate juice.

In another embodiment, pomegranate dry composition may be formulated in nutraceutical compositions and be delivered in an oral or enteral dosage form. Such compositions may be administered orally or enterally employing dry form preparations containing the pomegranate dry composition. The preparation of the nutraceutical composition may optionally include one or a combination of suitable binders, carriers, disintegrants, excipient, lubricants, colorants, and diluents. Such nutraceutical composition optionally may comprise one or more additional coatings surrounding the core and/or the control releasing coat such as moisture barrier coats, enteric coats or coatings that affect the physical integrity and/or appearance of the nutraceutical composition.

The dosage used in the embodiments may be applied in any suitable form, such as bars, pills, capsules, gels, liquid, etc. A dosage unit may comprise a powder, solid or semisolid form, and more acceptable in a dosage form includes without limitation, caplets, capsules, gelatin coated capsule, granules, microparticles, microspheres, pills, powder, tablets, and other solid or semisolid formulations. The solid or semisolid dosage form preferably has a weight between 0.1 and 30 grams, more preferably between 0.2 and 10 grams. In the embodiments, a daily dosage of the preparation as used in the invention can include one or more pills, tablets or other dosage forms. Concentrated liquid forms are also contemplated and make be made by mixing in the powder or other forms of the polyphenol composition described herein. Alternatively or in addition the liquid concentrate itself can be produced from byproducts of the juice production process.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, silica, and hydrogenated vegetable oils.

The effective amount of a nutraceutical composition is the amount or dosage unit of the pomegranate dry composition sufficient to achieve the intended beneficial health results. Accordingly, the effective amount of the nutraceutical composition to be administered depends on considerations such as the dosage unit employed, the mode of administration, the period of treatment, the age, sex, and weight of the person treated and the nature and extent of the condition treated. The effective amount can readily be determined based upon standard techniques known to evaluate whether the intended effect of the composition has been achieved, by standard toxicity texts and by standard pharmacological assays.

According to an embodiment of the invention the enteral or oral administration of a nutraceutical composition including the pomegranate dry composition. As mentioned concentrated liquid forms are also feasible. Particularly suitable is the administration of a dosage or serving the nutraceutical composition containing the pomegranate dry composition. Capsule form is typically most well suited for easy consumption but all other alternatives are within the scope and spirit of the invention.

The following examples further illustrate the embodiments of the invention disclosed herein. These examples are provided only for purpose of illustrating the embodiments of the invention and do not limit the invention in any manner whatsoever unless specifically claimed.

EXAMPLE 1

Production of Pomegranate Dry Composition

The starting material for the production of the pomegranate dry composition is the pomegranate solids, which generally comprise the pericarp, the inner membrane and seed of the pomegranate. The pomegranate solids were obtained and collected after the primary juice from the arils has been substantially expelled or otherwise removed from the pomegranate by pressing, crushing, or other methods known to the art for extracting pomegranate juice.

The pomegranate solids were then transferred to three Reitz Mills with ⅜ inch screens. The material was milled to a fine puree and heated to approximately 125° F. This step, coupled with the following enzyme addition, assisted in breaking down the colloidal structure of the remaining pomegranate solids, thereby releasing the remaining soluble solids.

The mixture was heated to a temperature of about 125° F. for two hours. Three enzymes were added to the mixture: pectinase (Rohapect® DA6L), cellulase/pectinase (Rohapect® CL), and hemi-cellulase/pectinase (Rohapect® B1L). These enzymes were used to liberate the remaining pomegranate soluble solids, such as sugars, minerals, anthocyanins, and remaining polyphenols.

The mixture was then pumped from the extraction plant to the primary processing plant where it was held in the mash treatment tanks for approximately one hour. After one hour, 50-100 pounds of bentonite in a 125 gallon of water slurry, per 8,000 gallons of the mixture, was added for protein removal. The treated mixture was then passed through a Westphalia 755 Decanter for removal of solids. The residual insoluble material was discharged as waste. The liquid extract then exited the decanter and was filtered on Koch SUPER-COR® microfiltration membranes at a 500,00 Da molecular weight cut-off and then filtered again on Koch ultrafiltration membranes at a 100,000 or 200,000 Da molecular weight cut-off.

The filtered liquid extract was then applied to a Schmidt-Bretten rising-film plate evaporator. Initial heat on this step was about 140° F. In this step, the filtered liquid extract was concentrated to about 15° to 20° Bx.

The filtered liquid extract was maintained at the temperature of about 140° F. and then passed through a pre-heated 140° F. preparative column (4-foot diameter, 4-foot tall) packed with Amberlite™ FPX66 (Rohm and Haas, Philadelphia, Pa.) at the flow rate of two bed volumes an hour until the resins gets loaded. Any portions of liquid effluent that indicate bleed-through of polyphenols were collected for subsequent loading step.

After the load step, dilute aqueous alcohol (2% ethanol/$H_2O$) was passed through the preparative column at the flow rate of two bed volumes an hour to remove unbound material. Dilute aqueous alcohol effluent was discarded as a waste.

After the rinse step, concentrated aqueous alcohol (20% ethanol/$H_2O$) was applied to the resin and the liquid eluate containing polyphenols was collected. In an optional step, the liquid eluate was then entered through Arnold Holstein distillation unit to remove and recover alcohol. The recovered alcohol was reused for subsequent cycles of rinse and elution steps.

The liquid eluate was transferred into a tray and dried in an oven at about 70°-80° C. After drying step, the resulting eluate was in form of a dense powder, which was used in other embodiments of the invention.

EXAMPLE 2

Analysis of the Pomegranate Dry Composition

The pomegranate dry composition from Example 1 was analyzed using HPLC and MALDI-TOF. The pomegranate dry composition is qualitatively identical to that of pomegranate juice and differs only in having a higher proportional content of pomegranate polyphenols, primarily punicalagin and its isomers. See Table 1 for breakdown of polyphenols in 100 grams of the pomegranate dry composition powder.

TABLE 1

| Polyphenols | Total | Glucose Part | |
|---|---|---|---|
| Punicalagin (17% glucose) | 25.5 | 4.3 | Mean of the range (16-35%) |
| Punicalin (23% glucose) | 4.4 | 1.0 | Mean of the range (2.2-6.6%) |
| Free ellagic acid | 6.7 | 0.0 | Mean of the range (4.6-8.8%) |
| Other ellagitannins and gallotannins (23-27% glucose) | 53.4 | 13.4 | Determined by difference (range 55-75); mean glucose 25% |
| Unidentified | 10.0 | 10.0 | Assumed |
| Sum: | 100.0 | 28.7 | |

Once produced in accordance with one or more embodiments of the invention described herein the pomegranate dry composition comprises the following generalized specifications.

SPECIFICATIONS

| | |
|---|---|
| Chemical Classification | Organic, Nutritive |
| Physical Classification | Dried Fruit |
| Color | Red-Brown |
| Odor | Characteristic Tannin |
| Taste | Characteristic Tannin |
| Plant Part Used | Husk, Arils (Juice), and Fruit |
| Chemical Parameters | |
| Total Phenolics | >85% (UV adsorption std. to pomegranate polyphenols) |
| pH (1 g/100 ml water) | 3.0 to 5.0 |
| Heavy Metals (ppm) | Less than 1 ppm. |

TABLE 1-continued

| Physical Parameters | |
|---|---|
| Particle Size (wt. % retained on 60 mesh) | Less than 2%. |
| Bulk Density (g/cc) | 0.8 to 0.9 |
| Tap Density (g/cc) | 0.9 to 1.0 |
| Microbiological Assays: | |
| Total Plate Count (CFU/g) | <1,000 |
| Yeast (CFU/g) | <100 |
| Mold (CFU/g) | <10 |
| Total Coliforms (CFU/g) | <10 (none detected) |
| E. coli (CFU/g) | <10 (none detected) |
| Salmonella (CFU/g) | Negative in 25 grams. |
| Staph. aureus (CFU/g) | <10 (none detected) |

SHELF LIFE 18 months at or below 70 F in a sealed container.

PACKAGING 10 kg. in a double-lined plastic bag. Product should be stored in the original sealed container and tightly closed after usage.

One created the powder and liquid forms provide similar polyphenol components of one serving of pomegranate juice. One serving of pomegranate juice contains at least 800 mg total natural polyphenols (650 mg gallic acid equivalent, GAE) with expected variation from year to year and batch to batch. Pomegranate juice has been shown to have up to 4,370 mg/L or 1,049 mg/8 oz of punicalagin compounds by Cerda et. al., 2004. GAE underestimates the total polyphenol level because gallic acid is not optimized standard. A 1,000 mg capsule of powder made using the process described herein contains at least 800 mg natural polyphenol using a pomegranate polyphenol standard. The table below is illustrative:

TABLE 2

Polyphenols in the specialized powder are similar to pomegranate juice polyphenols minus most of the anthocyanins.

| | Pomegranate Powder/Liquid | | | | |
|---|---|---|---|---|---|
| | Pomegranate Juice mg/8 oz. juice | | Special Pomegranate Powder mg/1,000 mg | | |
| | #1 | #2 | Batch 1 | Batch 2 | Batch 3 |
| Anthocyanins | 67.6 | 76.7 | trace | trace | Trace |
| Gallagyl-type (punicalagins & punicalin) | 181.8 | 96.9 | 169.4 | 141.4 | 161.1 |
| Ellagic acid and derivatives | 26.4 | 37.2 | 27.6 | 33.1 | 35.9 |
| Other hydrolysable tannins | 720.9 | 627.0 | 593.0 | 665.5 | 663.1 |
| Total | 966.7 | 837.9 | 790.0 | 840.0 | 860.0 |

EXAMPLE 3

Subchronic Toxicity Study of the Pomegranate Dry Composition

A 28-day oral gavage study in rats was conducted at an outside laboratory. 10 male and 10 female rats per group were dosed with 0, 150, 700, or 1500 mg/kg/day of the pomegranate dry composition from Example 1. Samples of blood were collected for clinical pathology evaluation on test days 29 and 31-32, and were shipped to a laboratory for analysis and interpretation.

Complete blood counts, including reticulocytes, were determined on a Bayer® Advia 120 hematology analyzer or determined from microscopic evaluation of the blood smear. Wright-Giemsa-stained blood smears from all animals were examined microscopically for confirmation of automated results and evaluation of cellular morphology. Coagulation times were determined on a Sysmex® CA-1000 Coagulation Analyzer. The following parameters were determined: red blood count, hemoglobin, hematocrit, mean corpuscular volume, mean corpuscular hemoglobin, mean corpuscular hemoglobin concentration, red cell distribution width, platelet count, white blood cell count, differential white blood cell count, microscopic blood smear examination, absolute reticulocyte count, prothrombin time, and activated partial thromboplastin time.

Serum clinical chemistry parameters were determined on an Olympus® AU640 clinical chemistry analyzer to determine the following parameters: aspartate aminotransferase, alanine aminotransferase, sorbitol dehydrogenase, alkaline phosphatase, total bilirubin, urea nitrogen, creatinine, cholesterol, triglycerides, glucose, total protein, albumin, globulin, calcium, inorganic phosphorous, sodium, potassium, and chloride.

Remaining sera from 4 randomly chosen animals were pooled into 2 aliquots, frozen at approximately −80° C. and sent to a laboratory for comprehensive antibody screening as part of a routine health screen. Titers to the following pathogens or antigens were determined: Sendai virus, pneunomia virus of mice, rat coronavirus/sialodacryoadentitis virus, Kilham's rat virus, Toolan's H-1 virus, reovirus, *mycoplasma pulmonis*, rat parvovirus, parvovirus non-structural protein 1, and rat minute virus 1.

Statistical analysis of clinical pathology data was performed with significance at $p<0.05$. Separate analysis was performed on the data collected for each sex.

The summary of the results follows. The following adverse serum clinical chemistry changes occurred in rats dosed with 1500 mg/kg/day: increased bilirubin and decreased triglyceride concentration (males and females), decreased total protein due to decreased globulin concentration (males only), and decreased glucose concentrations (females only). There were no other adverse changes in clinical chemistry parameters and no adverse changes in hematology, or congulation parameters in male or female rats dosed with the pomegranate dry composition powder. Therefore, under the conditions of this study and for the clinical pathology parameters measured, the no-observed-effect level (NOEL) was 1500 mg/kg/day for males and females, based on the finding of adverse effects at higher doses.

EXAMPLE 4

Pomegranate Capsule

The method described below was employed to obtain an oral dosage unit in a form of a capsule exhibiting rapid disintegration characteristics in gastric acid.

About 1000 mg of the pomegranate from Example 1 and about 200 mg of maltodextrin, which is used as a flow agent, are intimately mixed for prior to filling in a capsule comprising of hydroxypropyl methylcellulose.

This amount provides the polyphenol content equivalent to an 8 oz. bottle of pomegranate juice. The purification process of Example 1 enables the requisite polyphenol dose in a single capsule.

EXAMPLE 5

Administering Pomegranate Capsules to Overweight Individuals

Pomegranate capsules prepared according to Example 4 were evaluated for dietary supplement use and safety in 88 overweight human individuals with increased waist size. Generally healthy male and female subjects recruited were overweight (above normal body mass index of 25 to 32) and had central obesity as evidenced by a waist circumference of ≥35 inches for female and ≥40 inches for male. Exclusions included confounding factors such as those who were being treated for chronic diseases related to oxidative stress such as diabetes or hypertension. Subjects were counseled to eat a low flavonoid diet for the duration of the study. Individuals with any changes in smoking status, or those taking any supplement or drugs that might interfere with adsorption of polyphenols were excluded. Subjects were divided into two groups, each at a different clinical study site ("Site A" and "Site B").

At the Site A, 64 subjects consumed either one or two pomegranate capsules per day. In order to maintain blinding, subjects in 1 pomegranate capsule a day received one bottle of placebo and one bottle of pomegranate capsules. 7 of the 64 subjects received only placebo throughout the trial to assess the incidence of adverse effects in a group receiving only placebo. At the Site B, 22 subjects consumed one pomegranate capsule per day.

Following a screening visit, subjects received dietary instruction as to avoidance of foods with strong antioxidant properties for the duration of the trial. Safety laboratory determinations were made at each of three visits. At visits subsequent to the screening visit, subjects were queried for any adverse events since the previous visit and any changes in concomitant medications. Vital signs were taken at each visit. Safety laboratories include CBC, chemistry, and urinalysis. Studies of antioxidant activity as evidenced by thiobarbituric acid reactive substances (TBARS) in plasma and paraoxonase 1 activity (PON1) were measured before and after pomegranate capsule supplementation.

The arylesterase activity of PON1 was measured using phenylacetate as substrate. The reaction mixture contained 1 ml of 1 mM phenylacetate in 9 mM of Tris/HCL containing 0.9 mM of CaCl2 at a pH of 8.0. To this was added 10 µl of a 10-fold dilution of the plasma sample. The increase in absorbance at 270 nm was read. The change in molar extinction coefficient was 1,310 M-1 cm-1. Assays were corrected for the small spontaneous hydrolysis of phenylacetate by subtracting the rate observed in a reaction mixture without the addition of plasma. Arylesterase activity is expressed in units per milliliter. One unit was defined as 1 µM of phenylacetate hydrolyzed per minute.

Plasma was assayed for TBARS by using 1,1,3,3-tetramethoxypropane as a standard. Plasma samples were stabilized upon collection and separation from packed cells by the addition of 1 µM butylated hydroxytoluene to prevent any further lipid peroxidation. They were assayed on the day of collection, or, if necessary frozen at −70° C. for a few days. The TBARS test measures lipid peroxidation products, including precursors that will continue to break down to yield malondialdehyde.

At the Site A, there was a formal assessment of adverse reactions and a comprehensive series of blood tests for toxicity by comparison to the control group receiving placebo (see Tables 3 to 6). No subject discontinued the study due to an adverse event and no serious adverse events were reported.

Eleven minor adverse events were reported by nine of the 64 randomized subjects at the Site A (see Table 3). These events were distributed between the two treatment groups. Two of 27 (7.4%) subjects in the low dose group reported minor adverse effects as did five of 28 (17.9%) high dose subjects. There were no qualitative or quantitative differences between treatment groups or by comparison to placebo. There were no apparent treatment-related changes in any of the chemistry, hematology or urinalysis laboratory results in the subjects at the Site A (see Tables 4 to 6).

At the Site B, 22 subjects (18 females, 4 males) completed the treatment. The study results at the Site B are presented separately, because this study was carried out during the late Fall when a number of holidays occurred. As a result, a significant increase in body weight (1.30 lb±1.95 lb, p=0.005) was observed during the study. Despite this weight gain, there was a decrease in both AST (−2.64±5.36 U/L, p=0.031) and ALT (−3.09±6.94 U/L, p=0.049) (see Table 7). Before adjusting for change in weight, TBARS levels showed a significant decrease between baseline and 4 weeks (−0.13±0.23 μM, p=0.011). After adjusting for change in weight, decrease in TBARS was still significant but changes in ALT and AST were no longer significant. With the adjustment for weight, free fatty acids (FFA) increased slightly (0.09 mmol/l, p=0.035). There were no changes in glucose, BUN, creatinine, lipids, insulin, c-peptide, paraoxonase-1 or electrolytes.

This study demonstrates in preliminary fashion that a pomegranate extract dietary supplement is safe when ingested by healthy human subjects in amounts of 2 pomegranate capsules per day for 28 days. No adverse events related to the dietary supplement consumption or changes in hematology, serum chemistry or urinalyses were observed. Preliminary evidence of a reduction in TBARS was seen in the subjects who were studied at the Site B.

No allergic reactions were observed in any of the 79 subjects who consumed the dietary supplement at the two clinical study sites.

Therefore, the studies conducted demonstrate both the safety of a pomegranate ellagitannin enriched dietary supplement in humans and suggest that there may be a demonstrable antioxidant effect observable in humans.

TABLE 3

Adverse Events Reported at the Site A

| Body System | Preferred Term | Number of Subjects (%) Placebo | Number of Subjects (%) 1 Capsule/Day | Number of Subjects (%) 2 Capsules/Day |
|---|---|---|---|---|
| Respiratory System | Cough | | 1 (11%) | |
| | Laryngopharyngeal Pain | | 1 (11%) | |
| | Bronchitis | | 1 (11%) | |
| | Nasopharyngitis | 1 (11%) | | |
| | Sinusitis | 1 (11%) | | |
| Central Nerv. Syst. | Headache | | | 1 (11%) |
| Blood | Anemia | | | 1 (11%) |
| Musculoskeletal | Hand Fracture | | | 1 (11%) |
| Vascular | Hematoma | | | 1 (11%) |
| | Superficial Thrombophlebitis | | | 1 (11%) |
| Skin | Herpes Simplex | | | 1 (11%) |
| No. with any AE | | 2 | 2 | 5 |
| % with any AE | | 22.2% | 7.4% | 17.9% |

TABLE 4

Electrolytes and Renal Function Laboratory Results (p-values)

| | | 1 Pomegranate Capsule/Day | | | | 2 Pomegranate Capsules/Day | | | | Placebo | | | |
|---|---|---|---|---|---|---|---|---|---|---|---|---|---|
| Test | Units | Baseline | SD | End of Study | SD | Baseline | SD | End of Study | SD | Baseline | SD | End of Study | SD |
| BUN | mg/dL | 14.11 | 2.34 | 13.56 | 2.46 | 13.71 | 2.45 | 13.67 | 2.79 | 12.67 | 3.56 | 11.56 | 2.27 |
| Creatinine | mg/dL | 0.84 | 0.12 | 0.86 | 0.13 | 0.84 | 0.09 | 0.82 | 0.11 | 0.76 | 0.08 | 0.77 | 0.08 |
| Potassium | mEq/L | 4.49 | 0.38 | 4.33 | 0.33 | 4.36 | 0.22 | 4.29 | 0.20 | 4.23 | 0.25 | 4.21 | 0.21 |
| Sodium | mEq/L | 140.74 | 1.71 | 138.88 | 1.73 | 140.21 | 1.76 | 138.70 | 1.39 | 140.22 | 1.19 | 140.11 | 1.26 |
| Chloride | mEq/L | 104.63 | 2.14 | 103.64 | 2.05 | 104.11 | 1.12 | 103.70 | 1.21 | 105.78 | 1.58 | 104.44 | 1.16 |
| Bicarbonate | mEq/L | 22.78 | 2.01 | 23.88 | 1.52 | 22.86 | 1.79 | 24.07 | 1.86 | 22.67 | 2.22 | 24.89 | 1.70 |
| Calcium | mg/dL | 9.32 | 0.33 | 9.36 | 0.30 | 9.32 | 0.30 | 9.33 | 0.25 | 9.19 | 0.28 | 9.36 | 0.27 |
| Uric Acid | mg/dL | 5.16 | 1.36 | 5.00 | 1.17 | 4.36 | 1.02 | 4.20 | 0.96 | 4.50 | 1.07 | 4.58 | 1.04 |

TABLE 5

Liver Function Laboratory Results (p-values)

| Test | Units | 1 Capsules/Day | | | | 2 Capsules/Day | | | | Placebo | | | |
|---|---|---|---|---|---|---|---|---|---|---|---|---|---|
| | | Baseline | SD | End of Study | SD | Baseline | SD | End of Study | SD | Baseline | SD | End of Study | SD |
| ALK PHOS | U/L | 67.59 | 16.54 | 67.68 | 17.11 | 70.71 | 11.93 | 72.52 | 13.28 | 69.00 | 13.78 | 69.33 | 14.07 |
| AST/GOT | U/L | 19.04 | 5.60 | 21.44 | 8.36 | 17.00 | 3.64 | 24.19 | 13.74 | 19.33 | 3.56 | 22.56 | 6.30 |
| ALT/GPT | U/L | 20.78 | 8.63 | 23.92 | 12.52 | 17.86 | 6.74 | 26.07 | 17.08 | 18.22 | 4.37 | 22.00 | 6.89 |
| Total Bilirubin | mg/dL | 0.58 | 0.19 | 0.57 | 0.15 | 0.66 | 0.20 | 0.59 | 0.17 | 0.58 | 0.18 | 0.53 | 0.11 |
| Total Protein | g/dL | 7.35 | 0.39 | 7.29 | 0.25 | 7.27 | 0.35 | 7.35 | 0.27 | 7.24 | 0.32 | 7.32 | 0.31 |
| Albumin | g/dL | 4.41 | 0.23 | 4.40 | 0.23 | 4.41 | 0.15 | 4.44 | 0.14 | 4.40 | 0.13 | 4.42 | 0.10 |
| Direct Bilirubin | mg/dL | 0.10 | 0.02 | 0.10 | 0.02 | 0.11 | 0.03 | 0.11 | 0.02 | 0.09 | 0.02 | 0.11 | 0.02 |

TABLE 6

Glucose and Triglycerides Laboratory Results (p-values)

| Test | Units | 1 Capsules/Day | | | | 2 Capsules/Day | | | | Placebo | | | |
|---|---|---|---|---|---|---|---|---|---|---|---|---|---|
| | | Baseline | SD | End of Study | SD | Baseline | SD | End of Study | SD | Baseline | SD | End of Study | SD |
| Glucose | mg/dL | 95.30 | 10.40 | 94.76 | 11.93 | 89.18 | 7.61 | 90.30 | 5.57 | 97.78 | 9.04 | 96.33 | 10.59 |
| Cholesterol | mg/dL | 215.26 | 27.99 | 209.52 | 27.50 | 205.39 | 28.42 | 210.85 | 36.18 | 212.11 | 29.23 | 207.11 | 21.88 |
| Triglyceride | mg/dL | 209.15 | 155.13 | 204.00 | 128.00 | 153.04 | 80.91 | 127.89 | 58.75 | 153.00 | 42.67 | 148.22 | 71.19 |
| HDL | mg/dL | 53.93 | 9.99 | 52.56 | 10.90 | 59.75 | 11.30 | 59.70 | 8.93 | 47.67 | 6.15 | 48.67 | 6.67 |
| LDL Direct | mg/dL | 148.44 | 29.58 | 139.76 | 29.87 | 137.89 | 26.24 | 144.52 | 32.13 | 152.78 | 37.48 | 150.75 | 30.00 |

TABLE 7

Results of Study at the Site B Demonstrating a Significant Decrease in TBARS Despite an Increase in Body Weight

| Variable | Baseline Mean ± SD | 30-days Mean ± SD | Change Mean ± SD (95% CI) | p-value |
|---|---|---|---|---|
| Weight (lbs) | 201.77 ± 55.27 | 203.07 ± 55.52 | 1.30 ± 1.95 (0.44, 2.17) | 0.005 |
| BMI (kg/m$^2$) | 33.36 ± 8.52 | 33.57 ± 8.51 | 0.21 ± 0.35 (0.05, 0.36) | 0.010 |
| TBARS (uM) | 1.02 ± 0.20 | 0.89 ± 0.21 | −0.13 ± 0.23 (−0.23, −0.03) | 0.011 |
| AST (U/L) | 25.45 ± 7.17 | 22.82 ± 5.93 | −2.64 ± 5.36 (−5.01, −0.26) | 0.031 |
| ALT (U/L) | 26.27 ± 14.17 | 23.18 ± 12.32 | −3.09 ± 6.94 (−6.17, −0.01) | 0.049 |
| BUN (mg/dL) | 12.86 ± 3.91 | 11.68 ± 3.09 | −1.18 ± 2.77 (−2.41, 0.05) | 0.059 |
| Creatinine (mg/dL) | 0.86 ± 0.13 | 0.88 ± 0.16 | 0.02 ± 0.11 (−0.03, 0.06) | 0.427 |

While the invention herein disclosed has been described by means of specific embodiments and applications thereof, numerous modifications and variations could be made thereto by those skilled in the art without departing from the scope of the invention set forth in the claims.

The invention claimed is:

1. An oral or enteral dosage unit containing phytochemicals from pomegranates comprising:
   a dry composition comprising polyphenols from pomegranate, said dry composition comprising between about 14% to about 16.9% punicalagins and punicalin by weight, between about 2.7% to about 3.6% ellagic acid by weight, and between about 59% to about 66.6% other hydrolysable pomegranate polyphenols by weight, wherein said dry composition is obtained by:
   providing an aqueous solution containing at least one pomegranate solid comprising polyphenols from pomegranate;
   removing said polyphenols onto a separation medium contained in a resin bed by passing said aqueous solution through said resin bed at a temperature ranging from about 100° F. to 140° F. and at a flow rate of between about 1 to about 3 bed volumes per hour;
   rinsing said separation medium with a dilute aqueous alcohol comprising less than about 5% by volume of alkanol to remove an unbound material;
   eluting said separation medium with an eluent to remove said polyphenols from said separation medium to obtain a mixture comprising said eluent and said polyphenols; and,
   drying said mixture to produce said dry composition.

2. The oral or enteral dosage unit of claim 1 wherein said pomegranate solids comprise at least one element selected from the group consisting of pericarp, inner membrane, and seeds.

3. The oral or enteral dosage unit of claim 1 wherein said separation medium comprises any one or more polymers selected from a group consisting of polydivinylbenzene, polystyrene, polyvinyl chloride, polyethylene, and polymethylmethacrylate.

4. The oral or enteral dosage unit of claim 1 wherein said separation medium comprises a macroreticular adsorptive resin providing hydrophobic interaction with said aqueous solution.

5. The oral or enteral dosage unit of claim 4 wherein said adsorptive resin is cross-linked styrene-divinylbenzene.

6. The oral or enteral dosage unit according to claim 5 wherein said aqueous solution is obtained by:
   dispersing pomegranate solids in an aqueous solution to create a pomegranate solids mixture;

adding enzymes to said pomegranate solids mixture to allow at least partial degradation of said pomegranate solids; and, filtering said aqueous solution from said pomegranate solids mixture.

7. The oral or enteral dosage unit of claim 1 wherein said dilute aqueous alcohol comprises less than 2% by volume of alkanol in water.

8. The oral or enteral dosage unit of claim 7 wherein the alkanol of said dilute aqueous alcohol is ethanol.

9. The oral or enteral dosage unit of claim 8, wherein said eluent is a concentrated aqueous alcohol of at least about 5% v/v having alkanol of 1 to 4 carbon atoms.

10. The oral or enteral dosage unit of claim 9 wherein said concentrated aqueous alcohol comprises ethanol.

11. The oral or enteral dosage unit of claim 10 wherein said concentrated aqueous alcohol comprises between about 5% v/v to about 20% v/v of ethanol in water.

12. The oral or enteral dosage unit of claim 11 wherein said separation medium is in the form of a preparative column.

13. The oral or enteral dosage unit of claim 12 wherein said drying said mixture to produce said dry composition includes the step of distilling said mixture to recover alcohol.

14. The oral or enteral dosage unit of claim 13 wherein said dosage unit is in a form of caplet, capsule, gelatin coated capsule, granule, microparticle, microsphere, pill, powder, or tablet.

15. The oral or enteral dosage unit of claim 1, further comprising at least one pharmaceutically acceptable carrier.

16. The oral or enteral dosage unit of claim 1, wherein said dry composition comprises at least 85% phenolics by weight.

17. The oral or enteral dosage unit of claim 16, wherein said phenolics comprise between about 16% to about 35% punicalagin.

18. The oral or enteral dosage unit of claim 1, wherein said separation medium is selected to preferentially adsorb polyphenols minus anthocyanins.

* * * * *